United States Patent [19]

Baacke et al.

[11] Patent Number: 4,861,937

[45] Date of Patent: Aug. 29, 1989

[54] CATALYSTS FOR CONVERTING ALCOHOLS AND/OR ALIPHATIC ETHER TO UNSATURATED HYDROCARBONS AND PROCESS FOR THEIR PRODUCTION

[75] Inventors: Michael Baacke, Hanau; Klaus Deller, Hainburg; Peter Kleinschmit, Hanau; Edgar Koberstein, Alzenau, all of Fed. Rep. of Germany

[73] Assignee: Degussa Aktiengesellschaft, Frankfurt am Main, Fed. Rep. of Germany

[21] Appl. No.: 518,402

[22] Filed: Jul. 29, 1983

[30] Foreign Application Priority Data

Jul. 29, 1982 [DE] Fed. Rep. of Germany ....... 3228269

[51] Int. Cl.$^4$ ........................... C07C 1/00; C07C 1/20
[52] U.S. Cl. .................................. 585/640; 585/469; 585/639; 585/733
[58] Field of Search ................ 585/639, 733, 640, 469

[56] References Cited

U.S. PATENT DOCUMENTS

| | | | |
|---|---|---|---|
| 4,104,151 | 8/1978 | Rubin et al. | 208/120 |
| 4,423,274 | 12/1983 | Daviduk et al. | 585/640 |
| 4,441,990 | 4/1984 | Huang | 585/640 |

OTHER PUBLICATIONS

Kokotailo, "Pentasil Family of High Silica Crystalline Materials," Chem. Soc. Spec. Publ. vol. 33, pp. 133–139, 1980.

*Primary Examiner*—H. M. S. Sneed
*Assistant Examiner*—Chung K. Pak
*Attorney, Agent, or Firm*—Cushman, Darby & Cushman

[57] ABSTRACT

Alcohols and/or aliphatic ethers are converted to hydrocarbons employing catalysts consisting of crystalline aluminum silicate, a compound of zinc and/or cadmium and additional silica. The catalyst is produced by treating a crystalline aluminum silicate, in a given case, partially or completely converted into the hydrogen form with a zinc or cadmium compound and shaping with a silica containing binder.

18 Claims, No Drawings

CATALYSTS FOR CONVERTING ALCOHOLS AND/OR ALIPHATIC ETHER TO UNSATURATED HYDROCARBONS AND PROCESS FOR THEIR PRODUCTION

CROSS REFERENCE TO RELATED CASE

The catalysts per se and their method of preparation are claimed in our copending application Ser. No. 06/518,403 filed on July 29, 1983 and entitled "Catalyst For The Production Of Hydrocarbons And Process For Their Production" (Docket 1211), the entire disclosure of which is hereby incorporated by reference and relied upon.

BACKGROUND OF THE INVENTION

The invention is directed to a method of converting alcohols and unsaturated ethers to unsaturated hydrocarbons, especially to a mixture containing olefins and aromatics employing special catalysts.

A large increase in the production of synthetic fibers, synthetic resins and rubbers articles has occurred in recent years. Not the least cause of the increase is that the corresponding petrochemical raw matertials such as ethylene, benzene, toluene, and xylene would be available cheaply in increasing amounts. Additionally, there is an increasing demand for aromatic hydrocarbons which as additives in gasoline contribute to increasing the resistance to knocking.

The increasing demand for olefins such as e.g. $C_2$–$C_3$ olefins and aromatic hydrocarbons makes it desirable to find methods by which these hydrocarbons can be produced without relying upon petroleum. It is known to produce this type of hydrocarbon mixture which contains olefins and aromatic hydrocarbons from primary aliphatic alcohols, for example, methanol.

Thereby there is reacted a mixture of methanol and water on a ZnPdMgO-ZSM-5contact catalyst (see Chen U.S. Pat. No. 4,148,835, the entire disclosure of which is hereby incorporated by reference and relied upon including the United States patents mentioned therein).

The known process of Chen has the disadvantage that there can only be attained a maximum reaction of 71.1%. Since the reaction of the known process does not proceed to the maximum extent desired, there is need to develop a process which whill increase the reaction.

SUMMARY OF THE INVENTION

The object of the invention is a catalyst for converting alcohols and/or aliphtic hydrocarbons to unsaturated hydrocarbons consisting of (or consisting essentially of) crystalline aluminum silicate, at least one compound of the metals zinc and/or cadmium and also silica. The invention also includes the process of using the catalyst.

Of special interest as crystalline aluminum silicate is a zeolite. The zeolite can be of the structure type faujasite, mordenite and/or Pentasil (e.g., ZSM-5 and ZSM-11). Pentasil is described by Doelle et al in Journal of Catalysis, Volume 71, pages 27–40 (1981). The entire disclosure of the Doelle article is hereby incorporated by reference and relied upon.

In a further illustrative form of the invention, the zeolite can be employed in pretreated form. A preparation of this type, for example, can be an ion exchange, an impregnation, or a mixture with another component, preferably a compound of the metal, zinc and/or cadmium.

As metal, there is preferably present zinc. The supplementary silica can be present in the catalyst of the invention in amounts of 5 to 30 weight %, preferably 10 to 20 weight %, particularly 15 weight %, based on the aluminum silicate in powder form employed.

The zinc (and/or cadmium) content (calculated as ZnO or CdO) of the catalyst can be 0.1 to 30 weight %, preferably 0.5 to 3 weight %.

In a specific illustrative form, the zeolite used as aluminum silicate can have the following x-ray diffraction diagram with the following characteristic interferences:

| d-value | Int. |
| --- | --- |
| 11.17 ± 0.1 | 52 |
| 10.05 ± 0.1 | 35 |
| 6.34 ± 0.1 | 5 |
| 4.98 ± 0.03 | 4 |
| 4.35 ± 0.03 | 18 |
| 4.27 ± 0.03 | 23 |
| 3.85 ± 0.03 | 100 |
| 3.74 ± 0.03 | 54 |
| 3.66 ± 0.03 | 22 |
| 3.34 ± 0.03 | 8 |
| 2.98 ± 0.02 | 12 |
| 2.49 ± 0.02 | 12 |
| 2.00 ± 0.02 | 8 |

This type of zeolite which is of the type Pentasil can be produced by reaction of a mixture of water, sodium aluminate, sodium hydroxide, precipitated silica, and

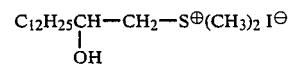

a temperature of 50° to 200° C. under autogenous pressure in an autoclave and subsequent conversion into the hydrogen form.

The conversion into the hydrogen form can be carried by a known treatment with acids, preferably with mineral acids such as, e.g., sulfuric acid, hydrochloric acid, or nitric acid.

Likewise, the conversion into the hydrocarbon can be carried out by exchange with ammonium ions and subsequent calcination.

The conversion into the hydrogen form can be carried out completely or partially. In a preferred illustrative form, the $Na_2O$ content of the crystalline aluminum silicate converted into the hydrogen form can be less than 0.1 weight %.

The template compound

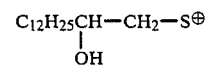

$(CH_3)_2I^\ominus$ used can be produced as follows:

Tetradecene oxide (1) is reacted in known manner with methyl mercaptan to the sulfide (2) and this product is reacted with methyl iodide to form the end product (3).

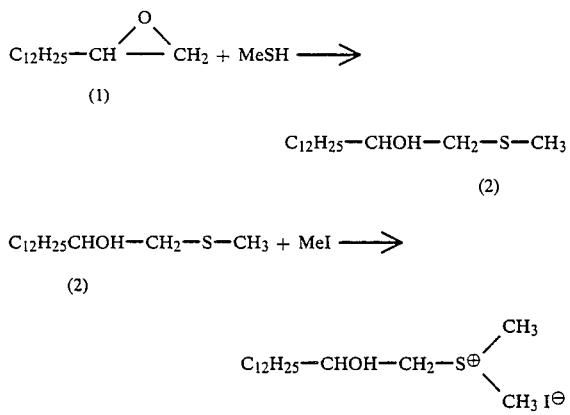

In a particular illustrative form, the catalyst of the invention can be present in shaped form, e.g., granulated, pelletized, extruded, or tabletted.

In the form, the catalyst, if the pretreatment is carried out with a zinc compound, can have the following compositions:
0.002 to 0.5 Wt.-% $Na_2O$
0.1 to 30 Wt.-% ZnO
0.4 to 5 Wt.-% $Al_2O_3$
60 to 98 Wt.-% $SiO_2$
2 to 15 Wt.-% Loss on calcining (DIN 51081)
For example, the composition can read as follows:
0.01 Wt.-% $Na_2O$
0.66 Wt.-% ZnO
1.39 Wt.-% $Al_2O_3$
91.51 Wt.-% $SiO_2$
5.4 Wt.-% Loss on calcining (DIN 51081)

Furthermore, the catalyst of the invention in shaped condition can have the following physical-chemical properties:
(a) BET-Surface area 539 $m^2/g$
(b) Hg-Compressed Volume 0.99 $cm^3/g$
(c) Sorption of n-Hexane 0.12 g/g, Benzene 0.06 g/g, 3-Methylpentene 0.09 g/g and water 0.06 g/g at $p/p_o=0.05$ and T=23° C.

A further object of the invention is the process for production of the catalyst for the conversion of alcohols and/or aliphatic ethers to unsaturated hydrocarbons which are characterized by treating a crystalline aluminum silicate, preferably of the Pentasil type, in a given case either partially or completely converted into the hydrogen form, with a metal compound and molding with a silicon dioxide binder.

The treatment of the crystalline aluminum silicate, preferably Pentasil, with a metal compound can be carried out through ion exchange with a metal salt solution, impregnation with a metal salt solution, or mixing with solid metal oxide.

As metal compounds, there can be employed the oxides and/or salts, as e.g., chloride, sulfate, nitrate, acetate, and others of zinc and/or cadmium.

The ion exchange can be carried out with an excess of zinc ions in aqueous solution in known manner. Thereby, there can be started with both the sodium form and also the hydrogen form of the crystalline aluminum silicate.

Since the sodium content of the catalyst preferably should be as low as possible, the impregnation (which term includes a drying) is carried out with aqueous zinc salt solution or the mixing with metal oxide preferably with a crystlline aluminum silicate or structural type Pentasil in the hydrogen form.

The amounts of metal compound added thereby corresponds to the final metal content of the crystalline aluminum silicate.

As silica containing binder, there can be employed in a preferred illustrative form silica sol or silica gel.

The molding of the crystalline aluminum silicate can take place accoding to known procedures.

For example, the molding can be carried out by addition of silica sol (40% silicon dioxide) to the aluminum silicate powder until reaching a moldable consistency and with subsequent shaping on a granulation plate. Likewise, a graunulation is possible through, e.g. extrusion.

The catalysts of the invention are employed for converting alcohols and/or aliphatic ethers to unsaturated hydrocarbons. At lower temperatures the alcohols can be converted to aliphatic ethers.

As alcohols there are primarily employed aliphatic alcohols, preferably having 1 to 4 carbon atoms. This type of alcohol includes for example, methanol, ethanol, propanol, isopropanol, butanol, sec.butanol and isobutanol which can be used alone or in admixture. Especially preferred is methanol, in a given case, in admixture with water.

As aliphatic ether there is preferably employed dimethyl ether. Other ethers include diethyl ether, dipropyl ether, dibutyl ether and diisopropyl ether.

The pressure used lies in the ranges that are known in the art, whereby in the selection of the operating pressure besides the purely reaction-kinetics factors there can also be considerred the pressure of the starting materials available. As especially suited, there has proven a total-reaction pressure of 1 to 100 bar, preferably of 1 to 30 bar.

The reaction temperature likewise can be varied within wide limits as in accordance with the state of the art, whereby a range of 200° to 500° C. and especially of 350° to 450° C. is preferred. It is an advantage of the process according to the invention that the conversion can be carried out at relatively high temperatures with excellent results.

The process according to the invention can be carried out with solid bed or fluidized bed catalyst. There can be employed the same reactors as are used according to the state of the art for conversion of synthesis gas. Examples of suitable reactors are those which are also employed for the methanol-synthesis, e.g., step reactors having cold gas addition, step reactors having intermediate cooling, tube reactors having internal or external cooling. The removal of heat is carried out according to the state of the art, e.g., by liquids or gases.

There can also be employed reactors such as are known for the Fischer-Tropsch synthesis; e.g. tube reactors, step reactors, fluidized bed reactors. A further possibility is reactors in which the heat of the reaction is removed from the reaction zone with the help of a recycled product gas.

An advantage of the invention is that at 100% reaction a hydrocarbon mixture is obtained which has a high olefin and a high aromatic portion.

Of especial advantage is that the hydrocarbon mixture, obtained according to the invention, has a low portion of paraffin hydrocarbons.

The catalyst can consist of, or consist essentially of the stated materials; and the process can comprise, consist essentially of, or consist of the stated steps with the recited materials.

DETAILED DESCRIPTION

Examples

A. Production of the Catalyst

Example 1

5 grams of sodium aluminate and 25 grams of NaOH were dissolved in 50 ml of $H_2O$ and added to a suspension of 200 grams of precipitated silica and 75 grams of $C_{12}H_{25}CHOHCH_2-S^{\oplus}(CH_3)_2I^{\ominus}$ in 2000 ml of $H_2O$. The mixture was stirred for 80 hours at 160° C. in an autoclave under autogeneous pressure, filtered off and washed to pH 9 with $H_2O$. The wet filter cake was suspended in 2 liters of ethyl alcohol, filtered off, washed with ethyl alcohol, and dried at 120° C. 100 grams of the dried silicate were stirred in 1 liter of 2 normal HCl for 2 hours at 80° C., filtered off, washed with water until neutral, and dried at 120° C.

Analysis: 0.06% $Na_2O$, 1.74% $Al_2O_3$, 91.1% $SiO_2$, 3.2% Loss on Calcining.

The aluminum silicate had an x-ray diffrac-characteristic interferences:

d-Value Int.
11.17±0.1 52
10.05±0.1 35
6.34±0.1 5
4.98±0.03 4
4.35±0.03 18
4.27±0.03 23
3.85±0.03 100
3.74±0.03 54
3.66±0.03 22
3.45±0.03 7
3.34±0.02 8
2.98±0.02 12
2.49±0.02 12
2.00±0.02 8

Example 2

50 grams of aluminum silicate according to Example 1 were stirred in a solution of 136.3 grams of $ZnCl_2$ in 500 ml of $H_2O$ for one hour at 80° C., filtered off, washed with water, and dried. The zinc treated aluminum silicate obtained had the following composition:
0.01 Wt.-% $Na_2O$
1.63 Wt.-% $Al_2O_3$
92.5 Wt.-% $SiO_2$
0.74 Wt.-% ZnO

Example 3

50 grams of aluminum silicate according to Example 1 without acid treatment (0.75% $Na_2O$).1.52% $Al_2O_3$.89.6% $SiO_2$) were stirred in a solution of 500 grams of $ZnCl_2$ in 500 of water for two hours at 80° C. and subsequently worked up as described in Example 2.

The zinc treated aluminum silicate obtained had the following composition;
0.18 Wt.-% $Na_2O$
1.15 Wt.-% $Al_2O_3$
85.9 Wt.-% $SiO_2$
1.17 Wt.-% ZnO

Example 4

50 grams of aluminum silicate as described in Example 1 were suspended in a solution of 1.25 grams of $ZnCl_2$ in 100 ml of water and stirred for 2 hours at 80° C. The mixture obtained was dried at 50° C./50 mbar.

The zinc treated aluminum silicate obtained had the following composition:
0.03 Wt.-% $Na_2O$
1.54 Wt.-% $Al_2O_3$
89.7 Wt.-% $SiO_2$
1.5 Wt.-% ZnO

Example 5

50 grams of aluminum silicate according to Example 1 in the hydrogen form and 1.5 grams of ZnO were suspended in 100 ml of water and stirred for 2 hours at 80° C. The mixture obtained was dried at 50° C. and pressure at 50 mbar.

The zinc salt pretreated silicate obtained had the following composition:
0.04 Wt.-% $Na_2O$
1.70 Wt.-% $Al_2O_3$
89.6 Wt.-% $SiO_2$
2.9 Wt.-% ZnO

Example 6

The aluminum silicate employed as in Example 4 was treated analogously with an aqueous zinc acetate solution. Under otherwise identical conditions, there were used 4.3 grams of zinc acetate. The zinc salt pretreated aluminum silicate obtained was subsequently calcined at 440° C. and had the following composition:
0.02 Wt.-% $Na_2O$
1.26 Wt.-% $Al_2O_3$
88.5 Wt.-% $SiO_2$
3.1 Wt.-% ZnO

Example 7

50 grams of aluminum silicate as described in Example 1 were suspended in a solution of 2.55 grams of $CdSO_4$ in 100 ml of water and stirred for 2 hours at 80° C. The mixture obtained was dried at 50° C./50 mbar. The product had the following composition:
0.06% $Na_2O$
1.26% $Al_2O_3$
88.4% $SiO_2$
2.76% CdO

Example 8

Shaping 50 grams of pretreated powdery aluminum silicate according to Examples 1 to 7 were mixed with 15 ml of 40% silica sol and 15 ml of water to form a pasty composition and shaped in the granulating plate. After the drying (4 hours at 120° C.), the granulates were calcined at 440° C. and sieved. The fraction 0.5 to 1.5 mm was used for the reaction of the methanol.

B. Methanol Conversion

Example 1

The catalyst prepared according to Example A2 was first activated at 420° C. in an $N_2$ stream. Then methanol was led over the catalyst at reaction temperature. The further experimented conditions were chosen as follows:

Total pressure: 1.8 bar
Employed: $CH_3OH/N_2 = 1$ mole/mole
T = 250°–400° C.
LHSV = 0.4 $h^{-1}$ There was complete reaction to hydrocarbons. These were composed as follows:

| Yield of Product in Liquid %. | | | |
|---|---|---|---|
| | 250° C. | 350° C. | 400° C. |
| Methanol | — | 23.0 | 0.8 |
| Dimethyl ether | 98.9 | 42.0 | 0.4 |
| Methane | — | 0.3 | 1.3 |
| Ethylene | — | 6.6 | 14.9 |
| Ethane | — | 0.1 | 0.4 |
| Propene | — | 6.4 | 15.0 |
| Propane | — | 0.2 | 0.5 |
| Isobutane | — | 2.5 | 1.4 |
| n-Butene | — | 2.1 | 5.6 |
| n-Butane + Butene-2 | — | 4.5 | 5.6 |
| n-Pentane | 0.6 | 0.1 | 0.1 |
| Isopentane | — | 1.5 | 1.5 |
| Pentene-2 | — | 0.9 | 4.2 |
| Cyclopentane | — | — | 0.1 |
| Iso-$C_6$—Hydrocarbons | — | 1.8 | 5.0 |
| Benzene | — | — | 0.7 |
| $C_7$—Hydrocarbons | 0.1 | 1.3 | 1.9 |
| Toluene | 0.3 | 0.4 | 4.2 |
| $C_8$—Hydrocarbons | — | 1.1 | 2.7 |
| Xylene | — | 2.4 | 14.4 |
| $C_9$-$C_{11}$—Hydrocarbons | — | 2.8 | 19.2 |

Example 2

Comparison Example

To convert $CH_3OH$ there was employed the zeolite powder prepared according to Example A1 with the single difference that it was not impregnated with the zinc salt solution but underwent all the same subsequent treatments.

The reaction conditions were selected as in Example B1. There was produced thereby complete reaction to hydrocarbons. These were composed as follows:

| Yield of Product in Liquid %: | | | |
|---|---|---|---|
| | 250° C. | 350° C. | 400° C. |
| Methanol | 8.1 | — | — |
| Dimethyl ether | 11.1 | — | — |
| Methane | 0.5 | 0.3 | 0.6 |
| Ethylene | 11.0 | 2.3 | 3.8 |
| Ethane | 0.1 | 0.2 | 0.4 |
| Propene | | 1.6 | 5.2 |
| Propane | 8.2 | 8.4 | 10.1 |
| Isobutane | — | | 12.1 |
| n-Butene | 11.4 | 17.2 | 4.6 |
| n-Butane + Butene-2 | 4.7 | 6.1 | 7.3 |
| n-Pentane | — | — | — |
| Isopentane | 10.1 | 9.4 | 7.4 |
| Pentene-2 | 1.2 | 3.2 | 3.5 |
| Cyclopentane | 12.1 | 0.4 | 0.9 |
| Iso-$C_6$—Hydrocarbons | — | 9.8 | 7.8 |
| Benzene | 0.2 | 0.9 | 1.7 |
| $C_7$—Hydrocarbons | 8.4 | 4.2 | 2.5 |
| Toluene | 1.3 | 8.5 | 9.2 |
| $C_8$—Hydrocarbons | 4.1 | 2.5 | 1.3 |
| Xylene | 3.1 | 12.6 | 12.2 |
| $C_9$-$C_{11}$—Hydrocarbons | 4.5 | 12.5 | 9.2 |

Example 3

To convert $CH_3OH$ there was used the zeolite powder prepared according to Example A7 which was shaped according to Example 8.

The reaction conditions corresponded to Example B1. The temperature selected was 350° C.

| Yield of Product in Wt. % | |
|---|---|
| | 350° C. |
| Methanol | — |
| Dimethyl ether | — |
| Methane | 2.8 |
| Ethylene | 13.9 |
| Ethane | 0.8 |
| Propene | 7.0 |
| Propane | 2.0 |
| Isobutane | 1.9 |
| n-Butene | 5.0 |
| n-Butane + Butene-2 | — |
| n-Pentane | — |
| Isopentane | 3.9 |
| Pentene-2 | 2.7 |
| Cyclopentane | — |
| iso-$C_6$—Hydrocarbons | 5.5 |
| Benzene | 0.4 |
| $C_7$—Hydrocarbons | 2.9 |
| Toluene | 4.7 |
| $C_8$—Hydrocarbons | 2.8 |
| Xylene | 13.7 |
| $C_9$-$C_{11}$—Hydrocarbons | 25.8 |

The entire disclosure of German priority application P3228269.9 is hereby incorporated by reference.

What is claimed is:

1. In a process for the production of hydrocarbons from an alcohol or an aliphatic ether in the presence of a catalyst which contacts the alcohol or ether, the improvement comprising employing a catalyst consisting essentially of (1) crystalline aluminum silicate in the hydrogen form modified with (2) a cadmium compound or a mixture of compounds of both zinc and cadmium, and (3) additional silica and thereby forming a product having a high olefin and lower portion of paraffin hydrocarbons;
    wherein the amount of cadmium is 0.1 to 30% by weight cadmium calculated on CdO and the amount of silica is 5–30% by weight 5 to 30% silica based on the amount the aluminum silicate.

2. A process according to claim 1 wherein said alcohol is methanol.

3. A process according to claim 1 wherein the catalyst contains said mixture of compounds of both zinc and cadmium.

4. A process according to claim 1 wherein the catalyst contains 0.5 to 3% cadmium calculated as CdO and contains 10 to 20% silica based on the amount the aluminum silicate.

5. A process according to claim 1 wherein the crystalline aluminum silicate is a zeolite.

6. A process according to claim 5 wherein the zeolite is a zeolite that has been pretreated by ion exchange with a compound of zinc or cadmium.

7. A process according to claim 5 wherein the zeolite is faujasite, mordenite, or Pentasil.

8. A process according to claim 7 wherein the zeolite has an x-ray diffraction diagram as follows:

| d-value | Int. |
|---|---|
| 11.17 ± 0.1 | 52 |
| 10.05 ± 0.1 | 35 |
| 6.34 ± 0.1 | 5 |
| 4.98 ± 0.03 | 4 |
| 4.35 ± 0.03 | 18 |
| 4.27 ± 0.03 | 23 |
| 3.85 ± 0.03 | 100 |
| 3.74 ± 0.03 | 54 |
| 3.66 ± 0.03 | 22 |

-continued

| d-value | Int. |
|---|---|
| 3.45 ± 0.03 | 7 |
| 3.34 ± 0.02 | 8 |
| 2.98 ± 0.02 | 12 |
| 2.49 ± 0.02 | 12 |
| 2.00 ± 0.02 | 8 |

9. A process according to claim 8 wherein the zeolite is one produced by reacting a mixture of water, sodium aluminate, precipitated silica, and

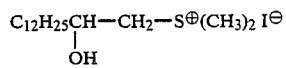

at a temperature of 50° to 200° C. under autogeneous pressure in a closed container followed by conversion into hydrogen form.

10. A process according to claim 7 wherein the zeolite is one produced by reacting a mixture of water, sodium aluminate, precipitated silica, and

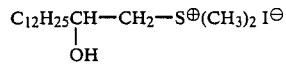

at a temperature of 50° to 200° C. under autogeneous pressure in a closed container followed by conversion into hydrogen form.

11. A process according to claim 1 carried out at a pressure of 1 to 100 bar and a temperature of 200° to 500° C.

12. A process according to claim 11 carried out at a pressure of 1 to 30 bar and a temperature of 350° to 450° C.

13. A process according to claim 1 carried out at a temperature of 200° to 500° C.

14. A process according to claim 4 carried out at a temperature of 200° to 500° C.

15. A process according to claim 6 carried out at a temperature of 200° to 500° C.

16. A process according to claim 1 wherein the temperature is 350° to 450° C.

17. A process according to claim 4 wherein the temperature is 350° to 450° C.

18. A process according to claim 1 wherein said alcohol is a 1 to 4 carbon atom alkanol, and said ether is a lower dialkyl ether.

* * * * *